United States Patent
Bremer et al.

(10) Patent No.: US 11,395,902 B2
(45) Date of Patent: Jul. 26, 2022

(54) SYSTEM AND METHOD FOR WAKING A USER UP WITH A STIMULUS OF VARYING INTENSITY

(71) Applicant: KONINKLIJKE PHILIPS N.V., Eindhoven (NL)

(72) Inventors: Petrus Johannes Bremer, Drachten (NL); Giulia Costa, Drachten (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/952,434

(22) Filed: Nov. 19, 2020

(65) Prior Publication Data
US 2021/0146089 A1    May 20, 2021

(30) Foreign Application Priority Data

Nov. 20, 2019   (EP) .................... 19210251

(51) Int. Cl.
*G08B 21/06* (2006.01)
*A61M 21/00* (2006.01)
(Continued)

(52) U.S. Cl.
CPC ........... *A61M 21/00* (2013.01); *G08B 5/36* (2013.01); *G08B 21/06* (2013.01); *A61B 5/4809* (2013.01);
(Continued)

(58) Field of Classification Search
CPC ....... A61B 5/16; A61B 5/4806; A61B 5/4809; A61B 5/4815; A61M 2021/0027; A61M 2021/0044; A61M 2021/0083; A61M 21/00; A61M 2205/3306; A61M 2205/332; A61M 2205/3368; A61M 2205/3375;
(Continued)

(56) References Cited

U.S. PATENT DOCUMENTS 8,781,796 B2   7/2014  Mott et al.
10,083,397 B2  9/2018  Yuan et al.
(Continued)

FOREIGN PATENT DOCUMENTS

WO   2008090494 A1   7/2008
WO   2010035200 A1   4/2010
(Continued)

OTHER PUBLICATIONS

Gimenez, M. et al., "Effects of artificial dawn on subjective ratings of sleep inertia and dim light melatonin onset", Chronobiology International, University of Groningen, 2010.
International Search Report and Written Opinion, International Application No. PCT/EP2020/082313, dated Feb. 9, 2021.

*Primary Examiner* — Daniel Previl

(57) ABSTRACT

A system for waking a user up by a stimulus, wherein the stimulus is adapted to vary according to an intensity curve. A user interface is adapted to receive user preferences, such as a desired wake-up time and a preference indicator. The preference indicator indicates whether the user prefers to be more alert after waking up or to have a longer sleep. An alarm is used for providing a stimulus to the user and a processor is used for determining a stimulus intensity curve for the alarm. Determining the stimulus intensity curve is based on at least the user preferences.

20 Claims, 4 Drawing Sheets

(51) Int. Cl.
*G08B 5/36* (2006.01)
*A61B 5/00* (2006.01)

(52) U.S. Cl.
CPC .... *A61B 5/4815* (2013.01); *A61M 2021/0044* (2013.01); *A61M 2021/0083* (2013.01); *A61M 2205/3306* (2013.01); *A61M 2205/3368* (2013.01); *A61M 2205/3375* (2013.01); *A61M 2205/502* (2013.01); *A61M 2230/63* (2013.01)

(58) Field of Classification Search
CPC ...... A61M 2205/502; A61M 2205/505; A61M 2205/52; A61M 2209/01; A61M 2230/06; A61M 2230/63; G04C 11/00; G04C 19/02; G04G 21/025; G08B 21/06; G08B 5/36; H04M 1/72448; H05B 45/20; H05B 47/105; H05B 47/16; Y02B 20/40
USPC ... 340/575, 903–905, 925, 929, 990–995.11, 340/449, 506, 527, 539.12, 539.19
See application file for complete search history.

(56) References Cited

U.S. PATENT DOCUMENTS

| 2003/0095476 | A1* | 5/2003 | Mollicone | H05B 47/16 |
| | | | | 368/73 |
| 2011/0230790 | A1 | 9/2011 | Kozlov | |
| 2013/0208576 | A1* | 8/2013 | Loree, IV | G04G 11/00 |
| | | | | 368/256 |
| 2017/0065792 | A1* | 3/2017 | Bonvallet | G16H 50/50 |
| 2017/0188941 | A1* | 7/2017 | Brinkhaus | A61B 5/4821 |
| 2018/0060732 | A1* | 3/2018 | Yuan | G06N 5/02 |

FOREIGN PATENT DOCUMENTS

| WO | 2013090479 A2 | 6/2013 |
| WO | 2014057979 A1 | 4/2014 |
| WO | 2019055414 A2 | 3/2019 |

* cited by examiner

SYSTEM AND METHOD FOR WAKING A USER UP WITH A STIMULUS OF VARYING INTENSITY

CROSS-REFERENCE TO PRIOR APPLICATIONS

This application claims the benefit of European Patent Application No. 19210251.5, filed on 20 Nov. 2019. This application is hereby incorporated by reference herein

FIELD OF THE INVENTION

This invention relates to the field of personalized wake-up systems. It relates in particular to waking a user up with a stimulus, wherein the stimulus is adapted to vary according to a stimulus intensity curve based on user preferences.

BACKGROUND OF THE INVENTION

About one-third of a person's life is spent in sleep. Sleep is an important rest process. The body's immune system is repaired and strengthened during sleep, which can restore fatigued cells to normal physiological functions and restore mental and physical strength. As people's living and work pressures continue to increase, it has seriously affected people's sleep quality. When the quality of sleep is affected, it will affect people's health and affect people's lives and work. Therefore, improving sleep has become an urgent need of many people.

Human sleep is affected by a hormone called melatonin, which is secreted by the pineal gland in the human brain. It is this hormone that guides us to sleep and improves sleep quality. After nightfall, when light stimulation has decreased, the secretion of melatonin in the body increases. The amount of melatonin during the night directly affects the quality of sleep of a user. Light is known to have an effect on melatonin secretion. When light intensity is diminished, the amount of melatonin is increased.

Based on this principle, wake-up lights are able to improve the wake-up experience by gradually modulating light intensity and color to bring people to a natural wake-up and prepare the body to start the day.

Two main disadvantages of wake-up lights are usually encountered: people will wake-up too early, because the light intensity is already too high too early or increasing too fast and people will wake-up too late, because the light intensity is not bright enough at the requested wake-up moment or increasing too slowly.

It is also typical for an alarm to wake up the user up using sound. There are alarms which can create a volume profile for the alarm sound in order to smoothen the wake-up experience of the user. These devices have the same disadvantages as wake-up lights, in that users can wake up too early due to the volume of the alarm being too loud early on, or the user waking up late due to the volume of the alarm being too quiet at the desired wake-up time.

EP 2 122 420 A1 discloses a wake up stimulus control system, comprising a control unit arranged to receive a user-determinable wake up time input and to control at least one stimulus source wherein the stimulus source is controllable by the control unit in such a way that the stimulus source provides a gradually increasing stimulus output in dependence on said input wake up time.

US 2003/095476 A1 discloses a method and apparatus for a waking system that wakes an individual gradually over a period of time in order to promote the wellness of that individual. The user sets the system controller with a desired final wakeup time, which is the time that the user must be awake. When the actual time reaches a stimulus introduction time (i.e. some time prior to the desired final wakeup time), the system controller causes the introduction of stimulus.

US 2018/060732 A1 discloses a method for personalized intelligent wake-up system based on multimodal deep neural network comprises monitoring a sleeping status of a user; obtaining a current sleeping-stage of the user within a current time frame and a prediction of a next sleeping-stage of the user for a next time frame; correcting the current sleeping-stage of the user through combining the current sleeping-stage and the prediction of the next sleeping-stage; determining a wake up strategy for the current time frame.

WO 2010/035200 A1 discloses a light therapy technique includes gradually increasing or decreasing an intensity of light in a manner that approximates a change in light intensity during a natural light event, such as dawn or dusk.

US 2011/230790 A1 discloses a method for operating a sleep phase actigraphy synchronized alarm clock that communicates with a remote sleep database, such as an internet server database, and compares user physiological parameters, sleep settings, and actigraphy data with a large database that may include data collected from a large number of other users with similar physiological parameters, sleep settings, and actigraphy data.

WO 2014/057979 A1 discloses an electronic apparatus provided with an alarm clock function.

WO 2019/055414 A2 discloses a stress reduction and sleep promotion system that includes at least one remote device and an article for temperature conditioning a surface.

In some alarm devices, it is possible to change the settings for the intensity of the stimulus from the alarm in order to personalize the gradual increase of the stimulus. However, it is difficult for a user to know the exact intensity curve which suits them best for certain times, as the user usually does not remember the early moments of waking up.

Therefore, there is a need for a system which can personalize the stimulus intensity curve for a user in order to optimize the user wake-up experience.

SUMMARY OF THE INVENTION

The invention is defined by the claims.

According to examples in accordance with an aspect of the invention, there is provided a system for waking a user up by a stimulus, wherein the stimulus is adapted to vary according to an intensity curve, comprising:

a user interface adapted to receive user preferences, wherein the user preferences comprise:

a desired wake-up time; and a preference indicator, wherein the preference indicator indicates whether the user prefers to be more alert after waking up or to have a longer sleep;

an alarm for providing a stimulus to the user; and a processor for determining a stimulus intensity curve for the alarm based on the user preferences.

A user will indicate at what time they wish to wake up, termed a desired wake-up time, and whether they would prefer to have a longer time to sleep or feel more alert in the morning, termed a preference indicator, on a user interface. A processor then determines a stimulus intensity curve based on the desired wake-up time and the preference indicator.

The stimulus may vary according to an intensity curve from a minimum value to a maximum value over a time period, wherein the processor is for determining a suitable time period of the stimulus intensity curve based on the user preferences.

The system may further comprise a memory unit for storing historic sleep data of the user comprising at least historic real wake-up times and corresponding historic intensity curves, and wherein the processor is for determining an intensity curve for the alarm further based on the historic sleep data.

For example, if the user wishes to wake up at 7:15 am and has indicated they would prefer a longer sleep versus alertness when waking up, and the historic data indicates that the user tends to wake up earlier than 7:15 am when using a longer stimulus intensity curve, it might decide to provide a shorter stimulus intensity curve so that the user doesn't wake up much earlier than 7:15 am.

The user interface may be further adapted to receive as input response to a question to determine a Karolinska Sleepiness Scale, KSS, score of alertness of the user or other satisfaction level after waking up and store the score in the memory unit as historic KSS data.

Determination of a stimulus intensity curve for the alarm by the processor may further comprise:

estimating a KSS score or other satisfaction level for the user, at the desired wake-up time, for a plurality of reference stimulus intensity curves based on the historic sleep data of the user;

estimating the likelihood of the user waking up earlier than the desired wake-up time for a plurality of reference stimulus intensity curves from the historic sleep data; and determining a stimulus intensity curve based on analysis of the estimated KSS scores, the estimated likelihoods and the preference indicator.

For example, the user interface could ask the user a pre-determined question when the user wakes up to find the KSS score or alertness of the user. Other satisfaction level indications may be used. This data would be stored as historic KSS data or other satisfaction data. The historic data can then be used by the processor to estimate a score or level for the user at the desired wake-up time for different reference stimulus intensity curves. The likelihood of the user waking up early for different reference stimulus intensity curves is also estimated. These estimations can then be compared against the preference indicator to find which stimulus intensity curve matches the preference of the user.

The alarm may be a wake-up light and the stimulus intensity curve modulates the intensity of the light.

The stimulus intensity curve may further modulate the color of the light emitted by the wake-up light.

The stimulus intensity curve may simulate a sunrise.

The system may further comprise at least one sensor or input device for receiving sensor data or input data, wherein the processor is adapted to use the sensor data to determine the intensity curve, wherein the sensor or input device comprises one or more of (but not limited to):
a motion sensor for sensing when the user wakes up;
a sensor for detecting when the user falls asleep;
an ambient light sensor;
a temperature sensor;
a user input device; and
an ambient sound sensor.

The user interface may be further adapted to receive the real wake-up time from the user. Thus, the user may provide an input to the system as soon as they wake up, to provide feedback to the system to assist in learning the user response to different intensity curves. This may be achieved using the user input device.

The fall asleep time and wake-up time may be used to derive the sleep duration and/or the time in bed.

The system may also comprise at least one sensor for receiving sensor data, wherein the processor may be adapted to use the sensor data to determine the stimulus intensity curve, wherein the historic sleep data further comprises historic sensor data. This may be used to provide automated feedback in respect of the user's response to the intensity curve applied to the stimulus.

The sensors could be a motion sensor for sensing when the user wakes up, an ambient light sensor, a temperature sensor or an ambient sound sensor (microphone). The data from these sensors can be used in combination with the historic data to find the ideal wake-up curve for the user. For example if the user seems to wake up as soon as a certain threshold of ambient light or ambient sound occurs, the stimulus intensity curve could be chosen by the processor such that the threshold is not passed before the desired wake-up time.

The invention also provides a method for determining an intensity curve for a stimulus to be generated by an alarm, comprising:

receiving user preferences, wherein the user preferences comprise:
a desired wake-up time; and
a preference indicator which indicates whether the user prefers to be more alert after waking up or to have a longer sleep;

determining a stimulus intensity curve based on the user preferences.

There may additionally be modulation of sounds and colors to be generated as the stimulus.

The invention also provides a computer program comprising computer program code means which is adapted, when said computer program is run on a computer, to implement the method of determining an intensity curve for a stimulus.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
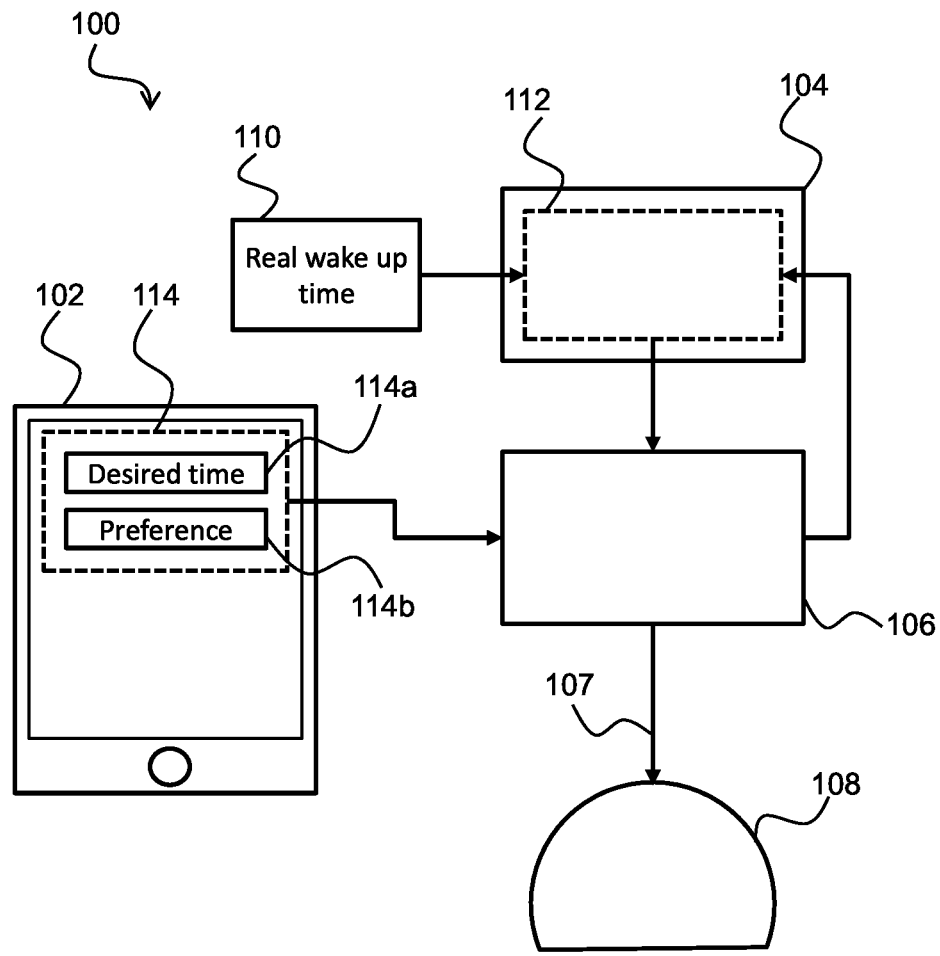
FIG. 1 shows a schematic representation of the system for waking a user up.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system for waking a user up by a stimulus, wherein the stimulus is adapted to vary according to an intensity curve. A user interface is adapted to receive user preferences, such as a desired wake-up time and a preference indicator. The preference indicator indicates whether the user prefers to be more alert after waking up or to have a longer sleep. An alarm is used for providing a stimulus to the user and a processor is used for determining a stimulus intensity curve for the alarm. Determining the stimulus intensity curve is based on at least the user preferences.

In an example, a memory unit is used for storing historic sleep data of the user. The historic sleep data includes historic real wake-up times and corresponding historic intensity curves. The alarm stimulus intensity curve is then also based on the historic sleep data.

FIG. 1 shows a schematic representation of a system 100 for waking a user up. A user will indicate a set of user preferences 114, including at what time they wish to wake up, termed a desired wake-up time 114a, and whether they would prefer to have a longer time to sleep or feel more alert in the morning, termed a preference indicator 114b, on a user interface 102. There is also a memory unit 104 which stores historic sleeping data 112 of the user. A processor 106 then determines an intensity curve 107 based on the historic sleeping data 112 and the user preferences 114. The intensity curve is sent to an alarm 108 to provide a stimulus to wake up the user. Once the user wakes up, the real wake-up time 110 of the user and the intensity curve 107 is stored in the memory unit 104 as historic sleep data 112.

The system 100 could be part of a mobile phone, where the user interface 102 is part of an application downloaded by the user on the mobile phone. The phone memory 104 and phone processor 106 could be used to determine the intensity curve 107. The application could then communicate with an external alarm 108, such as a wake-up light, or the phone could use the built-in speaker as the alarm 108, where the volume of the alarm is dependent on the intensity curve 107. The application could also determine two different curves, one for an external wake-up light and one for the built-in speaker.

Figure 2A:
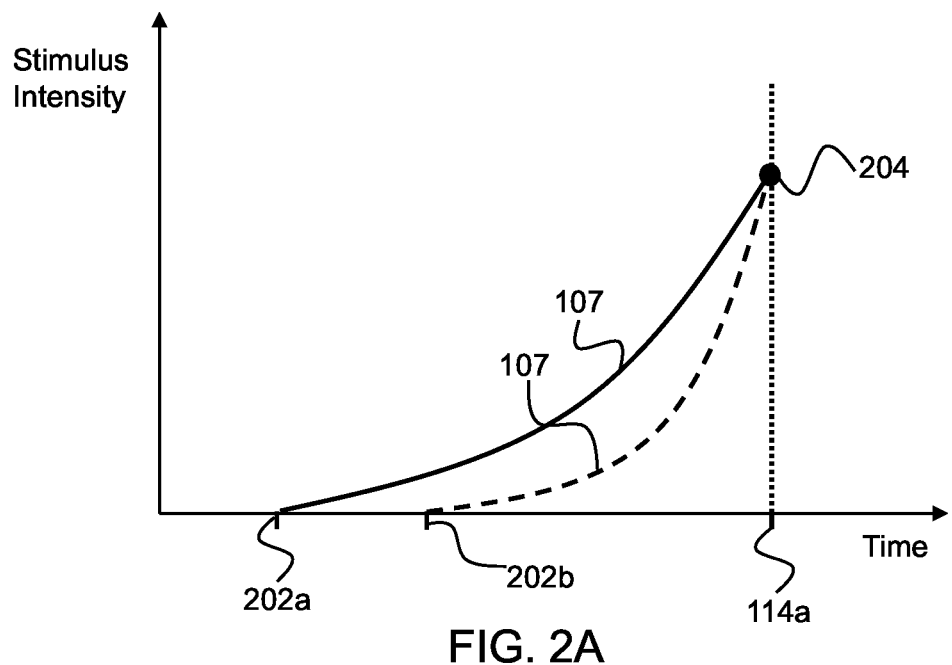
FIGS. 2A and 2B show graphical representations of the stimulus intensity curves.
Figure 2B:
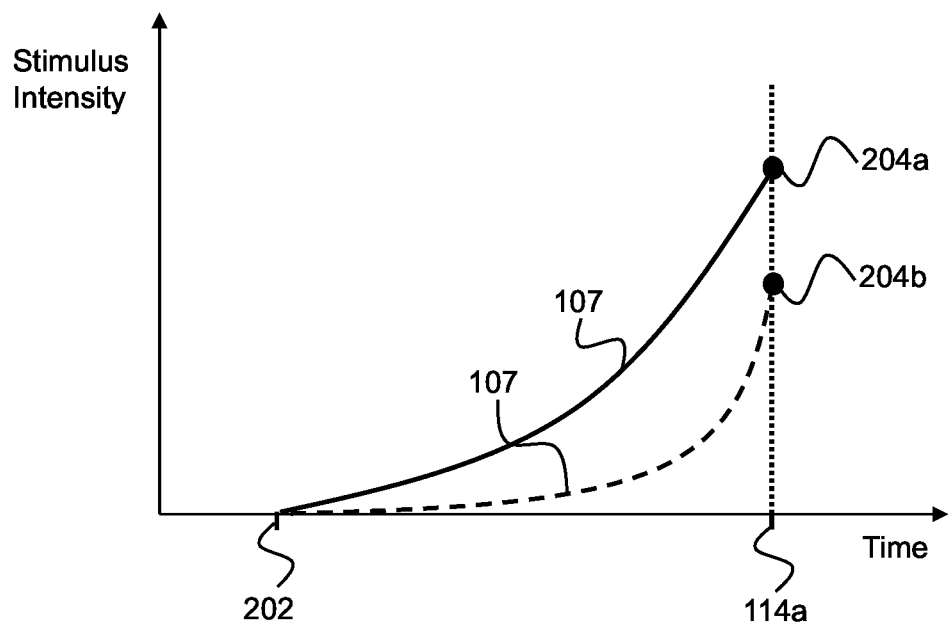

FIGS. 2A and 2B show graphical representations of the intensity curves 107. The stimulus may vary from a minimum value to a maximum value over a time period according to the stimulus intensity curve.

In conventional alarms 108, sound is used as a stimulus to wake up a user. Alternatively, light can also be used a stimulus, such as in wake-up lights, which increase the light intensity near or at the desired wake-up time, creating a natural wake-up experience.

It is expected that there is no correlation between light intensity curves 107 and sleep patterns, i.e. sleep stages, depth of sleep or EEG signals. However, there is a clear correlation between the length of the wake-up light curve 107 and the alertness in the morning: longer light curves 107 lead to a more alert state, while the use of shorter light curves 107 leads to more sleepiness.

It is also known that longer light curves 107 increase the chance of waking up too early and having a larger variability in the wake-up moment itself. Shorter light curves 107 on the other hand will wake up people closer to the desired wake-up time 114a, meaning the duration of sleep is maximized, but the chance of oversleeping increases.

A personalized setting prevents or at least diminishes these disadvantages while maintaining the natural wake-up experience and improving the well-being when waking up for the day ahead.

This means a personalized balance between a more alert wake-up experience, but shorter sleep i.e., waking up too early (with long curves) and a longer night, so possibly a better overall satisfied sleep experience, but a less alert wake-up experience (with short curves).

The personalized balance helps to overcome the negative effects on the user's satisfaction of waking up too early or too late with the right algorithm based on the personal user's preferences 114. It also allows the user to select an option (with long curves) which reduces the probability of oversleeping.

FIG. 2A shows a graphical representation of two different intensity curves 107. If a user wants to wake up in a more alert state, it may be beneficial to have a longer intensity curve 107 which starts earlier 202a, but may have a higher probability of waking the user up early. If the same user wants to have a longer sleep on a different day, an intensity curve 107 with a later start 202b may provide the user with a longer sleep, but with the possibility of a less alert wake-up experience.

FIG. 2B shows a second graphical representation of two different intensity curves 107 with different peak light intensities 204. A user may be waking up earlier than expected due an intensity curve 107 with a high peak light intensity 204a. It may be beneficial to reduce the peak light intensity to 204b, such that the light intensity during which the user typically wakes up happens later in time, closer to the desired wake-up time 114a.

There may also be separate intensity curves 107 while also the light color is modulated, when using a wake-up light. For example, the light color could start with a red tone and move to yellow and white tones near the desired wake-up time 114a. The intensity curves 107 could simulate a sunrise.

Figure 3:
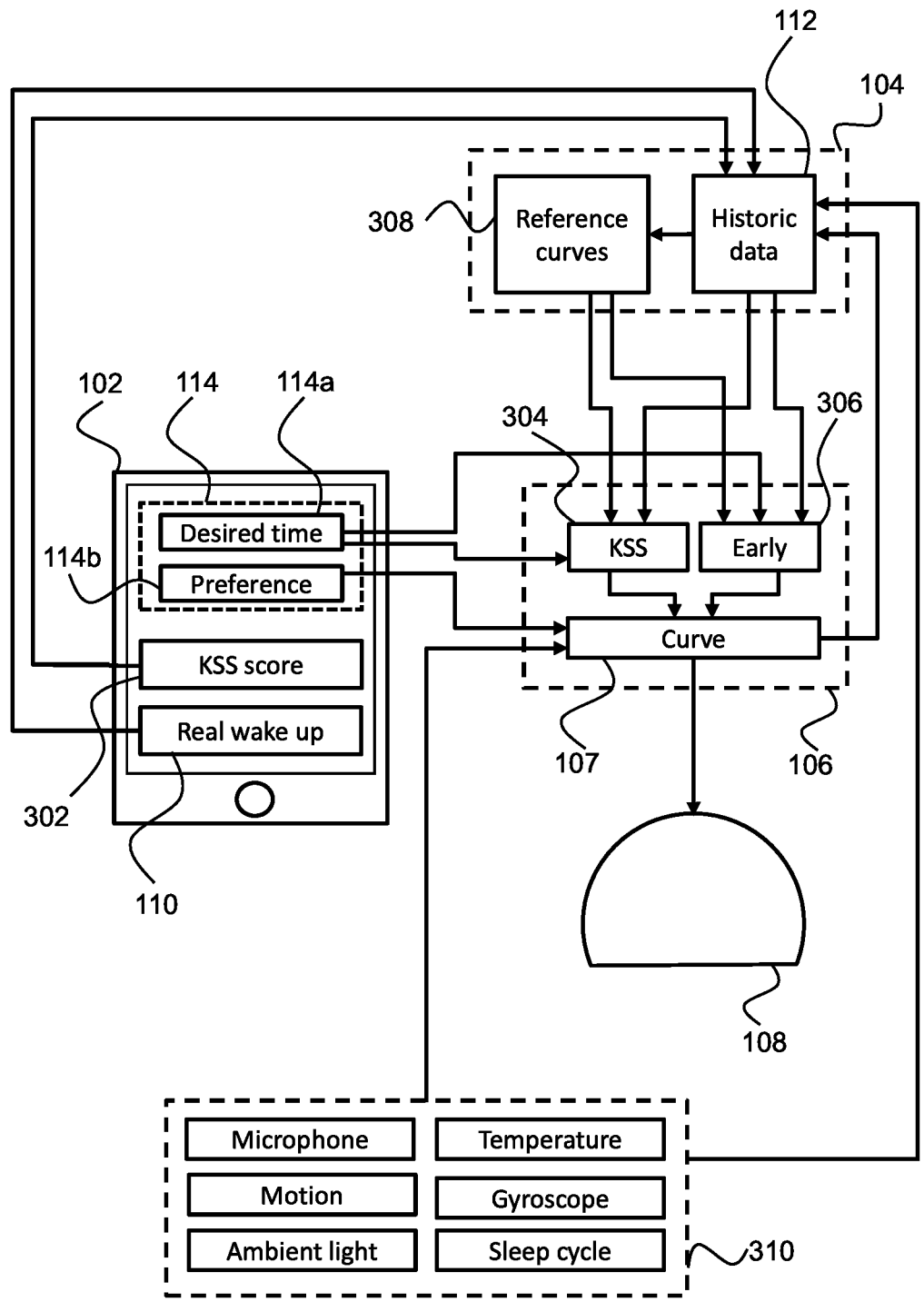
FIG. 3 shows a second schematic representation of a system for waking a user up.

FIG. 3 shows a second schematic representation of a system 100 for waking a user up. Similarly to FIG. 1, the user interface 102 is configured to receive the user preferences 114. Additionally, the user interface 102 can be further adapted to find the level of alertness for the user at the wake-up time. The level of alertness may be assessed by using the KSS (Karolinska Sleepiness Scale). For example, the user interface 102 could ask the user a question when the user wakes up to find the KSS score 302 of the user. The data can then stored as historic sleep data 112 in the memory unit 104.

Any other user indication relating to their satisfaction of their wake-up experience may be used. There may be one or more questions for the user to respond to, in order to assess their satisfaction level. The specific example of the KSS score is described below, simply by way of example.

The preference indicator 114b can then be determined by asking the user whether they prefer a better KSS score 302 with more chance to wake up early or less chance to wake up early and a lower KSS score.

The user may also indicate the real wake-up time 110 on the user interface 102. Alternatively an external sensor 310, such as a motion sensor, can indicate the real wake-up time 110.

The processor 106 predicts, based on the historic sleep data 112 for a number of reference stimulus intensity curves 308, the likelihood of a user waking up early 306 and the most likely KSS score 304 the user will experience at wake-up. This information is used in combination with the selected user preference 114b to determine the most suitable intensity curve 107.

The historic sleep data 112 may include the real wake-up time 110 for the user every morning, the past intensity curves 107 and the historic KSS scores 302. The memory unit 104 may also contain the reference stimulus intensity curves 308.

The processor 106 can also take into account the measured amount of light or even the expected amount of light in the bedroom due to the sun rising by using ambient light sensors.

Thus, many different types and combinations of sensors 310 could be used to aid the processor 106 in determining an intensity curve 107. The sensors 310 include, but are not limited to: a motion sensor for sensing when the user wakes up, an ambient light sensor, a temperature sensor or an ambient sound sensor (microphone). The data from the sensors 310 can be saved on the memory unit 104 as historic sleep data 112. The data from these sensors 310 can be used in combination with the historic sleep data to find the ideal intensity curve 107 for the user for different experiences, such as when the blinds are left open during the night. For example if the user seems to wake up as soon as a certain threshold of ambient light or ambient sound occurs, the intensity curve 107 could be determined by the processor 106 such that the threshold is not passed before the desired wake-up time 114a.

In another example, the user's amount of time in bed and temperature in the bedroom may also be determined using motion sensors and thermometers. The user may be more likely to wake up early at certain temperature ranges or during longer sleep duration, so the intensity curve 107 may be shortened in these circumstances.

The processor 106 could trigger a wake-up light alarm 108 and a speaker 108 simultaneously with different intensity curves 108. The curve for the wake-up light 108 could be determined, in part, by an ambient light and/or the predicted ambient light at the desired wake-up time 114a. The intensity curve 107 for the speaker 108 could be determined, in part, from the ambient sound sensed by a microphone.

Then, based on the user preferences 114, the historical sleep data 112 and the data from the sensors 310, the processor chooses the appropriate start time 202, shape and peak intensity 204 of the intensity curve 107 for the next wake-up cycle.

It is a fully adaptive and smart control algorithm to optimize the personal wake-up experience.

The historical sleep data 112 may also be used to alter and/or add reference stimulus intensity curves 308. For example, the curves with the associated KSS scores 302 and real wake-up times 110 which are closest to the preference 114b indicated by the user may be used in future as the reference stimulus intensity curves 308.

If the application is downloaded on a wearable device, such as a smart watch, the sensors 310 of the wearable device could be used for additional data. For example, the gyroscope of the device could be used to sense movement of the user. A heart rate monitor in conjunction with other sensors, such as a microphone and/or gyroscope, could be used to find the sleep stage the user is in. The sleep stage could then be used by the processor 106 of the wearable device to determine an intensity curve 107. For example, it may not be desirable to exceed a certain intensity of light and/or sound when the user is in deep sleep.

Figure 4:
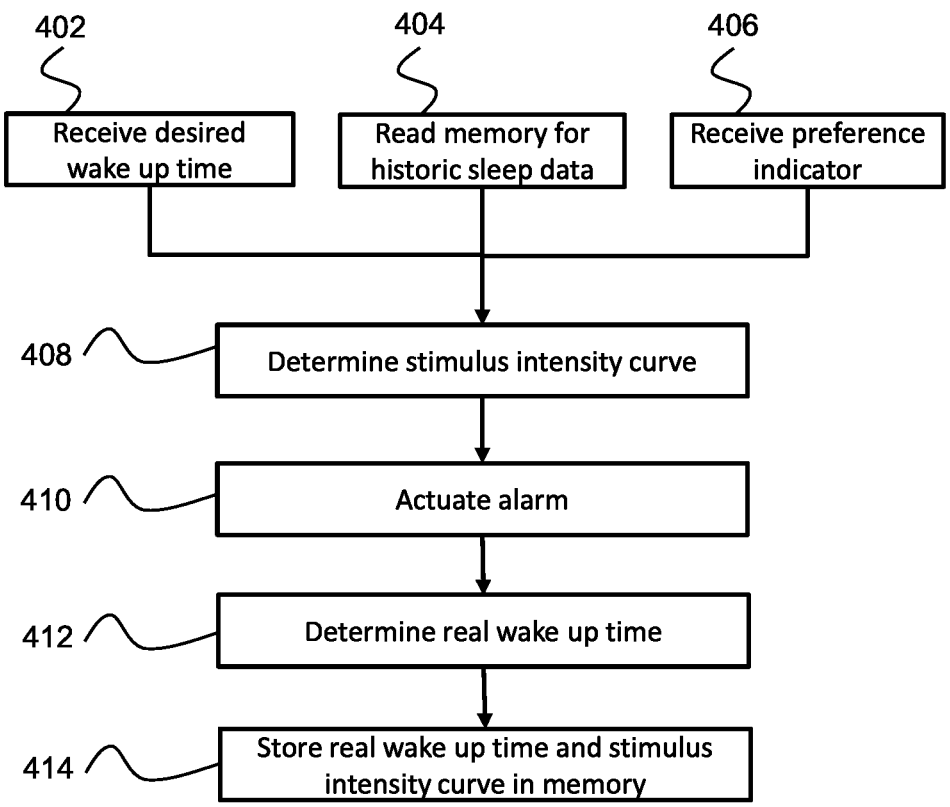
FIG. 4 shows a flow diagram of the method used by the processor to determine a stimulus intensity curve to be generated by an alarm.

FIG. 4 shows a method used by a processor 106 to determine an intensity curve 107 to be generated by an alarm 108. The method comprises first receiving user preferences from the user in steps 402 and 406. Receiving the user preferences comprises receiving a desired wake-up time, in step 402, and receiving a preference indicator, in step 406, which indicates whether the user prefers to be more alert after waking up or to have a longer sleep. The processor 106 also reads historic sleep data from a memory unit in step 404. Based on the user preferences and the historic sleep data, the processor then generates a stimulus intensity curve in step 408. The alarm is then actuated in step 410 to wake up the user. A real wake-up time is then determined, in step 412, at the time the user wakes up in response to the corresponding stimulus from the alarm, and the real wake-up time and the corresponding stimulus intensity curve are stored in a memory unit as historic sleep data in step 414.

FIGS. 2A and 2B show a gradual increase in the stimulus intensity, with increasing steepness (gradient) over time, so that there is a more rapid increase in intensity as the desired wake-up time is approached. Other shapes for the intensity curve are possible. For example, there may be flat regions and more abrupt step increases in intensity. There may for example be a step increase in intensity at the end of the curve to ensure a more reliable wake-up at the desired wake-up time, if the user has not already woken up (and turned off the alarm) by then.

For color control, there may be a decrease in intensity for some colors and an increase in intensity for others. The overall intensity curve of the stimulus (i.e., light) may therefore have multiple stimulus components which combine to create the desired overall effect.

The determination of the intensity curve may involve adapting the shape in a more complex way than the simple stretching represented in FIGS. 2A and 2B.

The example described above makes use of historical information so that the response of the individual user to different alarm stimuli may be taken into account. However, in a most basic implementation there is a set of alarm stimuli, i.e. intensity curves, and the processor selects the most appropriate an intensity curve based on the preference indicator.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A system for waking a user up by a stimulus, wherein the stimulus is adapted to vary according to an intensity curve, comprising:
a user interface adapted to receive user preferences, wherein the user preferences comprise:
a desired wake-up time; and
a preference selection, wherein the preference selection is one of
a selection to be more alert after waking up with a higher probability of waking up earlier than the desired wake up time, or
a selection to have a longer sleep by being closer to the desired wake up time with a higher probability of being less alert after waking up;
an alarm for providing a stimulus to the user wherein the stimulus varies according to an intensity curve from a minimum value to a maximum value over a time period; and
a processor configured to select one of a plurality of reference stimulus intensity curves having a start time and a peak intensity for the alarm based on the desired wake-up time and the preference selection.

2. The system as claimed in claim 1, further comprising a memory unit for storing historic sleep data of the user comprising at least historic real wake-up times and corresponding historic intensity curves, and wherein the processor is configured to select the one of the plurality of reference stimulus intensity curves based on the historic sleep data.

3. The system as claimed in claim 2, wherein the user interface is further adapted to determine a Karolinska Sleepiness Scale, KSS, score or other satisfaction level of the user after waking up and store the score or level in the memory unit as historic sleep data.

4. The system as claimed in claim 3, wherein the processor is configured to:
estimate a KSS score or other satisfaction level for the user, at the desired wake-up time, for the plurality of reference stimulus intensity curves based on the historic sleep data of the user;
estimate the likelihood of the user waking up early, compared to the desired wake-up time, for the plurality of reference stimulus intensity curves from the historic sleep data; and
select the one of the plurality of reference stimulus intensity curves based on analysis of the estimated KSS score or satisfaction level, the estimated likelihood of the user waking up early and the preference selection.

5. The system as claimed in claim 1, wherein the alarm is a wake-up light and at least one of the plurality of reference stimulus intensity curves modulates the intensity and color of the light.

6. The system as claimed in claim 5, wherein at least one of the plurality of reference stimulus intensity curves simulates a sunrise.

7. The system as claimed in claim 1, further comprising at least one sensor or input device for receiving sensor data or input data, wherein the processor is adapted to use the sensor data to selected the one of the plurality of reference stimulus intensity curves, wherein the sensor or input device comprises one or more of:
a motion sensor for sensing when the user wakes up;
a sensor for detecting when the user falls asleep;
an ambient light sensor;
a temperature sensor;
a user input device; and
an ambient sound sensor.

8. The system as claimed in claim 1, wherein the user interface is further adapted to receive the real wake-up time from the user.

9. The system as claimed in claim 1, wherein there is no correlation between the plurality of reference stimulus intensity curves and user sleep stages.

10. The system as claimed in claim 1, wherein there is a plurality of light color modulation curves for at least one of the plurality of reference stimulus intensity curves.

11. The system as claimed in claim 10, wherein there is a decrease in intensity for at least one color and an increase in intensity for at least one other color.

12. The system as claimed in claim 1, wherein there is a step increase in intensity at the end of at least one of the plurality of reference stimulus intensity curves.

13. A method for determining an intensity curve for a stimulus to be generated by an alarm wherein the stimulus varies according to the intensity curve from a minimum value to a maximum value over a time period, comprising:
receiving user preferences, wherein the user preferences comprise:
a desired wake-up time; and
a preference selection, wherein the preference selection is one of:
a selection to be more alert after waking up with a higher probability of waking up earlier than the desired wake up time or
a selection to have a longer sleep by being closer to the desired wake up time with a higher probability of being less alert after waking up;
selecting one of a plurality of reference stimulus intensity curves having a start time and a peak intensity of the intensity curve based on the desired wake-up time and the preference selection.

14. The method as claimed in claim 13, further comprising storing historic sleep data of the user comprising at least historic real wake-up times and corresponding historic intensity curves, wherein the selecting of the one of the plurality of reference stimulus intensity curves is further based on the historic sleep data.

15. The method as claimed in claim 13, further comprising:
    determining a Karolinska Sleepiness Scale, KSS, score or other satisfaction level of the user after waking up; and
    storing the KSS score or other satisfaction level in the memory unit as historic sleep data.

16. The method as claimed in claim 15, wherein the selecting of the one of the plurality of reference stimulus intensity curves further comprises:
    estimating a KSS score or other satisfaction level, for the user at the desired wake-up time, for the plurality of reference stimulus intensity curves based on the historic sleep data of the user;
    estimating the likelihood of user waking up early, compared to the desired wake up time, for the plurality of reference stimulus intensity curves from the historic sleep data; and
    selecting of the one of the plurality of reference stimulus intensity curves based on analyzing the estimated KSS scores or other satisfaction levels, the estimated likelihood of the user waking up early and the preference selection.

17. The method as claimed in claim 13, further comprising receiving sensing data from at least one sensor or input data from an input device, wherein the sensor or input device comprises one or more of:
    a motion sensor for sensing when the user wakes up;
    a sensor for detecting when the user falls asleep;
    an ambient light sensor;
    a temperature sensor;
    a user input device;
    an ambient sound sensor,
    and wherein the method further comprises storing the sensing data or input data as part of the historic sleep data.

18. A computer program comprising computer program code means which is adapted, when said computer program is run on a computer, to implement the method of claim 13.

19. The method as claimed in claim 13, wherein there is a plurality of light color modulation curves for at least one of the plurality of reference stimulus intensity curves.

20. The method as claimed in claim 19, wherein there is a decrease in intensity for at least one color and an increase in intensity for at least one other color.

* * * * *